(12) United States Patent
Someya

(10) Patent No.: US 8,168,675 B2
(45) Date of Patent: May 1, 2012

(54) COMPOSITIONS AND METHODS FOR TREATING NEURODEGENERATIVE DISEASES

(75) Inventor: Shinichi Someya, Madison, WI (US)

(73) Assignee: Marin Bio Co., Ltd., Madison, WI (US)

( * ) Notice: Subject to any disclaimer, the term of this patent is extended or adjusted under 35 U.S.C. 154(b) by 593 days.

(21) Appl. No.: 12/347,746

(22) Filed: Dec. 31, 2008

(65) Prior Publication Data

US 2009/0169533 A1 Jul. 2, 2009

Related U.S. Application Data

(60) Provisional application No. 61/018,594, filed on Jan. 2, 2008.

(51) Int. Cl.
*A01N 37/44* (2006.01)
(52) U.S. Cl. .......................... 514/557; 514/561; 514/666
(58) Field of Classification Search .................. None
See application file for complete search history.

(56) References Cited

U.S. PATENT DOCUMENTS

| | | | |
|---|---|---|---|
| 5,919,823 A | 7/1999 | Richardson | |
| 5,977,162 A | 11/1999 | Seidman | |
| 6,080,788 A | 6/2000 | Sole | |
| 6,303,139 B1 | 10/2001 | Passi | |
| 2002/0177558 A1 | 11/2002 | Meyerhoff et al. | |
| 2003/0045541 A1 | 3/2003 | Bruckner et al. | |
| 2003/0055099 A1 | 3/2003 | Martynyuk et al. | |
| 2004/0024048 A1 | 2/2004 | Wessel | |
| 2005/0107338 A1 | 5/2005 | Seidman | |
| 2006/0078549 A1 | 4/2006 | Ferrante | |

OTHER PUBLICATIONS

Seidman, M D. et al, "Biologic activity of mitochondrial metabolites on aging and age-related hearing loss" American Journal of Otolaryngology, Mar. 2004, 21(2): 161-167.
Database Embase (Online) Elsevier Science Publishers, Amsterdam, NL; "Studies on diagnosis and treatment of perceptive deafness (Japanese)" & Therapeutique 1962, 16(6-7): 317-322.
Sato K, "Pharmacokinetics of coenzyme Q10 in recovery of acute sensorineural hearing loss due to phypoxia", Acta Oto-Laryngologica. Supplementum 1989; 107(458): 95-102.
Hirose Y et al., "Effect of water-soluable coenzyme Q10 on noise-induced hearing loss in guinea pigs" Acta Oto-Laryngologica. Supplementum 2008, 128(10): 1071-1076.
Someya et al., "Caloric restriction suppresses apoptotic cell death in the mammalian cochlea and leads to prevention of presbycusis" 2007 Neurobiol. Aging 20:1613.
Keithley et al., "Age-related hearing loss and the ahl locus in mice" 2004 Hear Es. 188:21.

*Primary Examiner* — Nashaat Nashed
(74) *Attorney, Agent, or Firm* — Casimir Jones, S.C.

(57) ABSTRACT

The present invention relates to compositions and methods for treating neurodegenerative diseases. In some embodiments, the present invention provides compositions for treating and preventing presbycusis.

5 Claims, 4 Drawing Sheets

Fig. 1. Study design.

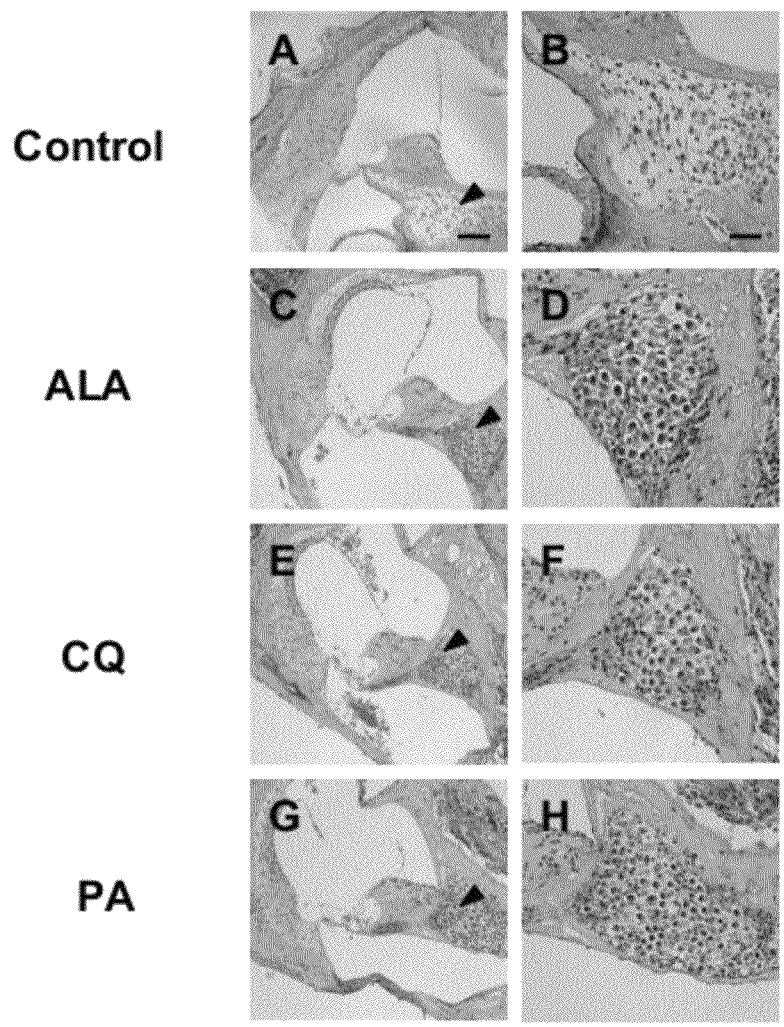
Fig.3. Photomicrographs of the Cochlea Basal Turn from Control (A-B), ALA (C-D), CQ (E-F), and PA (G-H) Mice.

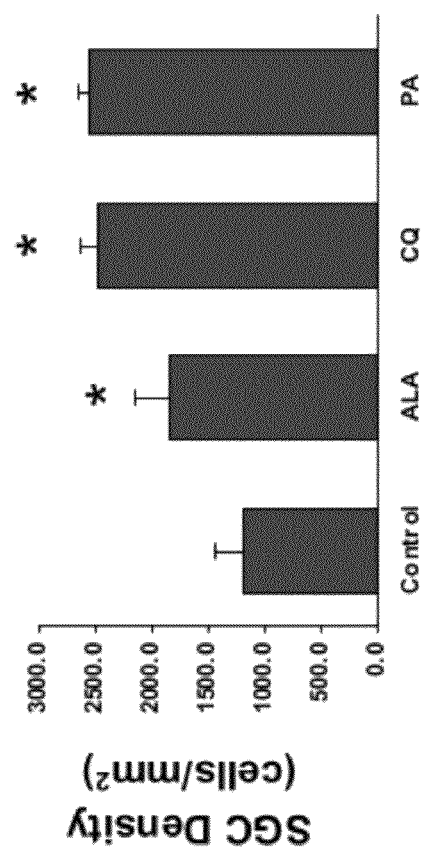
Fig. 4. Mean spiral ganglion cell density of Control, ALA, CQ, and PA mouse cochleae.

COMPOSITIONS AND METHODS FOR TREATING NEURODEGENERATIVE DISEASES

The present application claims priority to U.S. provisional application No. 61/018,594 filed Jan. 2, 2008, which is incorporated herein by reference in its entirety.

FIELD OF THE INVENTION

The present invention relates to compositions and methods for treating neurodegenerative diseases. In some embodiments, the present invention provides compositions for treating and preventing presbycusis.

BACKGROUND OF THE INVENTION

Age-related hearing loss or presbycusis poses enormous humanitarian and economic challenges to society. In the US, it is estimated that 23 percent of people aged between 65 and 75 years of age, and 40 percent of people over 75 years of age have presbycusis, and the number of people suffering from this disorder is expected to grow dramatically as the population of older people increases (Someya et al., Neurobiol. Aging 20:1613 [2007]).

Presbycusis is the loss of hearing that gradually occurs in most individuals as they grow older. Hearing loss is a common disorder associated with aging. The loss associated with presbycusis is usually greater for high-pitched sounds or high frequency sounds.

There are many causes of presbycusis. Most commonly it arises from pathological changes in the inner ear of a person as he or she ages, but presbycusis can also result from pathological changes in the middle ear or from complex pathological changes along the nerve pathways leading to the brain. Presbycusis most often occurs in both ears, affecting them equally. Because the process of loss is gradual, people who have presbycusis may not realize that their hearing is diminishing. With presbycusis, sounds often seem less clear and lower in volume. This contributes to difficulty hearing and understanding speech.

Sensorineural hearing loss is caused by disorders of the inner ear or auditory nerve. Presbycusis is usually a sensorineural hearing disorder. It is most commonly caused by gradual changes in the inner ear. The cumulative effects of repeated exposure to daily traffic sounds or construction work, noisy offices, equipment that produces noise, and loud music can cause sensorineural hearing loss. Sensorineural hearing loss is most often due to a loss of hair cells (sensory receptors in the inner ear). This can occur as a result of hereditary factors as well as aging, various health conditions, and side effects of some medicines (aspirin and certain antibiotics).

Presbycusis may be caused by changes in the blood supply to the ear because of heart disease, high blood pressure, vascular (pertaining to blood vessels) conditions caused by diabetes, or other circulatory problems. The loss may be mild, moderate, or severe.

Sometimes presbycusis is a conductive hearing disorder, meaning the loss of sound sensitivity is caused by abnormalities of the outer ear and/or middle ear. Such abnormalities may include reduced function of the tympanic membrane (the eardrum) or reduced function of the three tiny bones in the middle ear that carry sound waves from the tympanic membrane to the inner ear.

There are many strategies to help people with presbycusis. Hearing aids may be recommended for some individuals. Assistive listening devices can provide further improvement in hearing ability in certain situations. One example of such a device is the built-in telephone amplifier. Another example is FM systems that make sounds clearer, with or without a hearing aid, by delivering sound waves like a radio. Training in speechreading (using visual cues to determine what is being spoken) can help those with presbycusis to understand better what is being said in conversations or presentations.

Nonetheless, no preventative or therapeutic interventions have been developed for presbycusis.

SUMMARY OF THE INVENTION

The present invention relates to compositions and methods for treating neurodegenerative diseases. In some embodiments, the present invention provides compositions for treating and preventing presbycusis. In some embodiments, other neurodegenerative disease are treated. In some embodiments, the present invention provides nutritional supplements, food products, and pharmaceutical compositions, and methods for administering such products comprising compounds that prevent or reduce neurodegenerative diseases.

For example, in some embodiments, the present invention provides a method of treating a neurodegenerative disease, comprising: administering at least one compound selected from α-lipoic acid (ALA), conjugated linoleic acid (CLA), coenzyme Q10 (CQ), or phenylalanine (PA) or derivatives, mimetics or analogues thereof to a subject having symptoms of a neurodegenerative disease under conditions such that the symptoms are reduced. In some embodiments, the one or more compounds is two compounds (e.g., ALA and CLA; ALA and CQ; ALA and PA; CLA and CQ; CLA and PA; or CQ and PA). In some embodiments, the one or more compounds is three compounds (e.g., ALA, CLA, and CQ; ALA, CLA and PA; CLA, CQ and PA; or ALA, CQ and PA). In some embodiments, the one or more compounds are ALA, CLA, CQ and PA. In some embodiments, any of the above are provided with one or more additional components (e.g., adjuvants, excipients, drugs, nutritional supplements, carriers, etc.). In some embodiments, the neurodegenerative disease is presbycusis. In other embodiments, the neurodegenerative disease is a neurodegenerative disease described herein. In some embodiments, the administration of the one or more compounds prevents or reduces loss of spiral ganglion cells in the subject.

The present invention further provides a method of preventing a neurodegenerative disease, comprising: administering at least one compound selected from ALA, CLA, CQ, or PA or derivatives, mimetics or analogs thereof to a subject under conditions such that neurodegenerative disease is prevented in the subject. In some embodiments, the administration of the one or more compounds prevents a decrease in levels of spiral ganglion cells in the subject.

The present invention additionally provides a food product comprising of or consisting of one or more compounds selected from ALA, CLA, CQ or PA or derivatives, analogs or mimetics thereof.

The present invention also provides a nutritional supplement comprising of or consisting of one or more compounds selected from ALA, CLA, CQ or PA or derivatives, analogs or mimetics thereof.

The present invention also provides a pharmaceutical composition comprising of or consisting of one or more compounds selected from ALA, CLA, CQ or PA or derivatives, analogs or mimetics thereof.

Additional embodiments of the present invention are described herein.

DESCRIPTION OF THE FIGURES

FIG. 3 shows photomicrographs of the cochlea basal turn from control, ALA, CQ and PA mice.

FIG. 4 shows mean spiral ganglion cell density of control, ALA, CQ and PA mouse cocleae.

DEFINITIONS

Figure 1:
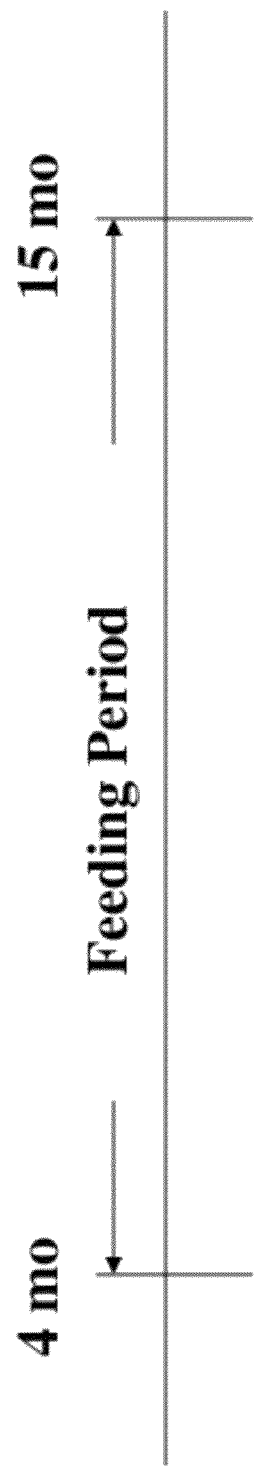
FIG. 1 shows the study design of some experiments conducted during the course of development of embodiments of the present invention.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reactions that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., hearing loss). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

"Prepared food product" means any pre-packaged food approved for human consumption.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed).

As used herein, the term "mimetic" refers to a small molecule compound that mimics the binding or interaction of a ligand with its target or mimics the physiological effect of the compound. For example, a mimetic of a compound described herein is a small molecule that has the same physiological effect as the compound (e.g., prevention or treatment of neurodegenerative disease).

DETAILED DESCRIPTION OF THE INVENTION

The present invention relates to compositions and methods for treating neurodegenerative diseases.

Some embodiments of the present invention provide compositions, pharmaceutical compositions, food products, nutritional supplements and methods of administering the compositions for prevention and treatment of presbycusis.

Experiments conducting during the course of development of the present invention evaluated the effects of numerous dietary compounds and identified four compounds (α-lipoic acid (ALA), CLA, coenzyme Q10 (CQ), and phenylalanine (PA)) useful for prevention and treatment of neurodegenerative disease. For example, experiments were conducted in C57BL/6 (B6) mice, which have been used extensively as a model of presbycusis and show late onset of age-related hearing loss by 15 months of age (Keithley et al., Hear Res. 188:21 [2004]) and significant loss of SGCs and hair cells by 12 months of age (Keithley et al., [2004], supra).

I. Therapeutic Methods

In some embodiments, the present invention provides methods for prevention and treatment of neurodegenerative diseases, including but not limited to, presbycusis. For example, by administering one or more of the compounds described herein to a patient, one can prevent and/or treat diseases and coditions due to the effect of the compound. Likewise, an analogue or derivative of the compounds can be administered to a patient. Presbycusis arises mainly from the degeneration of hair cells or neuronal cells in the cochlea. The present invention is not limited to a particular mechanism. Indeed, an understanding of the mechanism is not necessary to practice the present invention. Nonetheless, both ALA and CQ are antioxidants and it is contemplated that they may protect cochlear cells from oxidative damage to a sufficient level to achieve the benefits described herein. PA (L-phenylalanine) can be converted into L-tyrosine, which in turn is converted into L-DOPA, which is further converted into dopamine, norepinephrine (noradrenaline), and epinephrine (adrenaline) that are required for neurotransmission in the cochlea. Caloric restriction (CR) completely prevented presbycusis in mammals (Someya et al., [2007], supra). CR mice stay lean and maintain body weight at the same level as that of young mice. CLA is a weight loss inducer and therefore is believed to mimic CR-like, anti-aging effects. Thus, providing one or a mixture of these compounds is another method to prevent and treat presbycusis due to the effects of the compounds. In some embodiments, the present invention further provides methods to prevent and treat other age-associated neurodegenerative diseases including, but not limited to, those described below.

A. Compositions

In some embodiments, the present invention provides one or more of α-lipoic acid (ALA), CLA, coenzyme Q10 (CQ), and phenylalanine (PA) for use in treating or preventing neurodegenerative diseases (e.g., presbycusis). Lipoic acid is essential for aerobic life. Lipoic acids acts as a cofactor in aerobic metabolism, specifically the pyruvate dehydrogenase complex. Lipoate participates in the transfer of acyl or methylamine groups sin 2-oxoacid dydydrogenase and glycine cleavage complexes. CLA refers to a family of isomers on linoleic acid. CLA is produced by microorganism in the rumen of ruminants. CQ is a benzoquinone. CQ is present in all human cells and is responsible for the production of all the body's own energy. 95% of the human body's ATP is converted with the aid of CQ. PA is an non-polar α-amino acid. PA is an essential amino acid that cannot be made by animals. PA is provided by plants and microorganisms from prephenate, an intermediate on the shikimate pathway.

In some embodiments, one of ALA, CLA, CQ or PA is provided in a composition for administration to a subject. In other embodiments, 2 of ALA, CLA, CQ or PA (e.g., ALA and CLA, ALA and CQ, ALA and PA, CLA and CQ, CLA and PA, or CQ and PA) is provided. In other embodiments, 3 or more of ALA, CLA, CQ or PA (e.g., ALA, CLA, and CQ, ALA, CLA and PA, CLA, CQ and PA, or ALA, CQ and PA) are provided. In still further embodiments, ALA, CLA, CQ and PA are provided.

In a preferred embodiment of the present invention, a safe and effective nutritional or therapeutic amount of one or more of ALA, CLA, CQ and PA is orally administered to an animal (including humans) to prevent or treat neurodegenerative disease (e.g. presbycusis). Because one or more of ALA, CLA, CQ and PA are non-toxic, naturally occurring products and not a drug, they may be consumed as a part of a normal diet and find use as a part of everyday nutrition in people wishing to treat or prevent neurodegenerative disease. A nutritionally or therapeutically effective amount is the amount, that, when ingested in purified form or as food supplement results in prevention of neurodegenerative disease or a reduction in symptoms of neurodegenerative disease.

In some embodiments, compounds of the present invention are administered one or more times per week up to one or more times per day for a human adult (e.g., in one or more equal or non-equal doses). In some embodiments, dosages are estimated from the dosages used in mouse studies. For example, assuming a 60 kg human adult, mouse doses in mg/kg are multiplied by 0.081 to acquire a Human Equivalent Doses (HED) in mg/kg according to FDA Guidelines.

For example, in some embodiments, ALA is administered at a dose of approximately 0.1 to 100 mg/kg or 6 to 6000 mg administered one or more times per day in one or more doses (e.g., 30 to 3000 mg, 15 to 1500 mg, or approximately 60 mg), CLA is administered at a dose of approximately 0.5 to 5000 mg/kg or 30 to 300,000 mg administered one or more times per day in one or more doses (e.g., 1000 to 100,000 mg, 1,500 to 150,000 mg, or approximately 3,000 mg), CQ is administered at a dose of approximately 0.03 to 33.3 mg/kg or 2 to 2000 mg administered one or more times per day in one or more doses (e.g., 10 to 1000 mg, 5 to 500 mg or approximately 20 mg), and PA is administered at a dose of approximately 0.2 to 166.6 mg/kg or 10 to 10,000 mg administered one or more times per day in one or more doses (e.g., 50 to 5000 mg, 25 to 2500 mg or approximately 100 mg), although higher or lower doses may be used.

It is anticipated that there will be some variation in effectiveness because of differences among individuals in parameters such as body weight, basal metabolism, exercise, and other aspects of the diet.

The present invention also contemplates the use of derivatives of ALA, CLA, CQ and PA. For example, the compounds may be free or bound through ester linkages. In some embodiments, CLA is provided in the form of an oil containing CLA triglycerides. In these embodiments, the triglycerides may be partially or wholly comprised of CLA attached to a glycerol backbone. The CLA may also be provided as a methylester or ethylester. Furthermore, the CLA may be in the form of a non-toxic salt, such as a potassium or sodium salt (e.g., a salt formed by reacting chemically equivalent amounts of the free acids with an alkali hydroxide at a pH of about 8 to 9). In other embodiments, further derivatives, mimetics and variants of ALA, CLA, CQ or PA may be utilized.

B. Administration

In some embodiments, administration is oral. The composition may be formulated with suitable carriers such as starch, sucrose or lactose in tablets, pills, dragees, capsules, solutions, liquids, slurries, suspensions and emulsions. The compositions of embodiments of the present invention may be provided in aqueous solution, oily solution, as or in any of the other forms discussed above. The tablet or capsule of embodiments of the present invention may be coated with an enteric coating which dissolves at a pH of about 6.0 to 7.0. A suitable enteric coating which dissolves in the small intestine but not in the stomach is cellulose acetate phthalate. In some embodiments, the compositions are provided as soft gelatin capsules. The compositions may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of Remington's Pharmaceutical Sciences (Maack Publishing Co., Easton, Pa.). In some embodiments, formulations include one or more of ALA, CLA, CQ or PA, alone or in combination in a single administration dose.

The ALA, CLA, CQ or PA compositions may also be provided as a supplement in various prepared food products and drinks. For the purposes of this application, prepared food product means any natural, processed, diet or non-diet food product to which one or more of ALA, CLA, CQ or PA has been added. The compositions may be directly incorporated into various prepared food products, including, but not limited to drinks, bars, supplements, prepared frozen meals, candy, snack products (e.g., chips), prepared meat products, milk, cheese, or yogurt.

In some embodiments, compositions are provided as a nutritional supplement (e.g., as a tablet, capsule, liquid, etc) alone or in combination with suitable excipients (e.g., those described above). In some embodiments, nutritional supplements are packaged in a container or bottle that includes instructions describing dosage and timing of administration of the supplements.

In some embodiments, compositions are packaged human use with suitable antioxidants such as lecithin, tocopherols, ascorbate, ascorbyl palmitate or spice extracts such as rosemary extract.

C. Diseases

The compositions and methods of the present invention are suitable for the treatment of any number of neurodegenerative diseases. For example, in some embodiments, the compositions and methods of the present invention find use in the treatment or prevention of presbycusis. In other embodiments, the compositions and methods of the present invention are used in the treatment of additional neurodegenerative diseases, including but not limited to, Alzheimer's disease, Parkinson's diseases, Huntington's disease, amyotrophic lateral sclerosis, Alexander disease, Alper's disease, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, HIV-associated dementia, Kennedy's disease, Krabbe disease, Lewy body dementia, Machado-Joseph disease (Spinocerebellar ataxia type 3), Multiple sclerosis, Multiple System Atrophy, Narcolepsy, Neuroborreliosis, Pelizaeus-Merzbacher Disease, Pick's disease, Primary lateral sclerosis, Prion diseases, Refsum's disease, Sandhoff disease, Schilder's disease, Subacute combined degeneration of spinal cord secondary to Pernicious Anaemia, Schizophrenia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, and Tabes dorsalis.

Experimental

The following examples are provided in order to demonstrate and further illustrate certain preferred embodiments and aspects of the present invention and are not to be construed as limiting the scope thereof.

Example 1

2. Materials and Methods 2.1. Animals and Dietary Manipulation

Details on the methods used to house and feed male inbred C57BL/6 (B6) mice have been described (Pugh et al., Cancer Res. 59:1642 [1999]). Briefly, Mice were divided into five groups: control, α-lipoic acid (ALA), CLA, coenzyme Q10 (CQ), and phenylalanine (PA). The compound treatment groups were fed the same caloric intake as controls, but were supplemented with ALA (150 mg/kg), CLA (5000 mg/kg), CQ (50 mg/kg), and PA (250 mg/kg) from 4 months of age until 15 months of age (FIG. 1).

2.2. Assessment of Hearing

Detailed protocols for ABR measurement have been described (Yamasoba et al., Neurosci Lett. 395:18 [2005]). Briefly, ABRs were measured with a tone burst stimulus (4, 8, and 16 kHz) using an ABR recording system (Intelligent Hearing System). Mice were anesthetized with a mixture of xylazine hydrochloride (10 mg/kg, i.m.) and ketamine hydrochloride (40 mg/kg, i.m.). Five to seven mice per group were used for this study, and the same mice were used for the following histopathological analyses. Data were examined using the two-tailed standard t-test and were tested for statistical significance using a One Way ANOVA test (GraphPad Prisim 5.0, San Diego, Calif.). All data were reported as mean±S.E.M.

2.3. Histopathological Analysis

Detailed protocols for tissue processing have been described (Someya et al., [2007], supra). Briefly, 4% paraformaldehyde-fixed and paraffin-embedded specimens were sliced into 4 μm sections, mounted on silane-coated slides, stained with Haematoxylin and Eosin (HE), and observed under a light microscope (Leica Microsystems, Bannockburn, Ill.). The Rosenthal's canal was divided into three regions: apical, middle and basal (Keithley et al., [2004], supra) and the three regions were used for evaluation of cochlear histopathology. Five mice were used for each group that were the same mice as those used in the ABR tests. Five modiolar sections obtained in every fifth section from one unilateral cochlea were evaluated per mouse. The same animals were used for spiral ganglion cell counting.

Spiral ganglion cells (SGCs) were counted in the apical, middle, and basal turn of the cochlear sections in the field of 0.3 μm×0.225 μm as seen using a 40× objective by direct observation. SGCs were identified by the presence of a nucleus. The SGC density was calculated as the number of SGCs per 1 mm$^2$. Five sections of the unilateral apical turn were evaluated in one cochlea per mouse. Data were analyzed using the two-tailed standard t-test. All data were reported as mean±S.E.M.

3. Results 3.1. Evaluation of Hearing Function and Cochlear Histopathology

Figure 2:
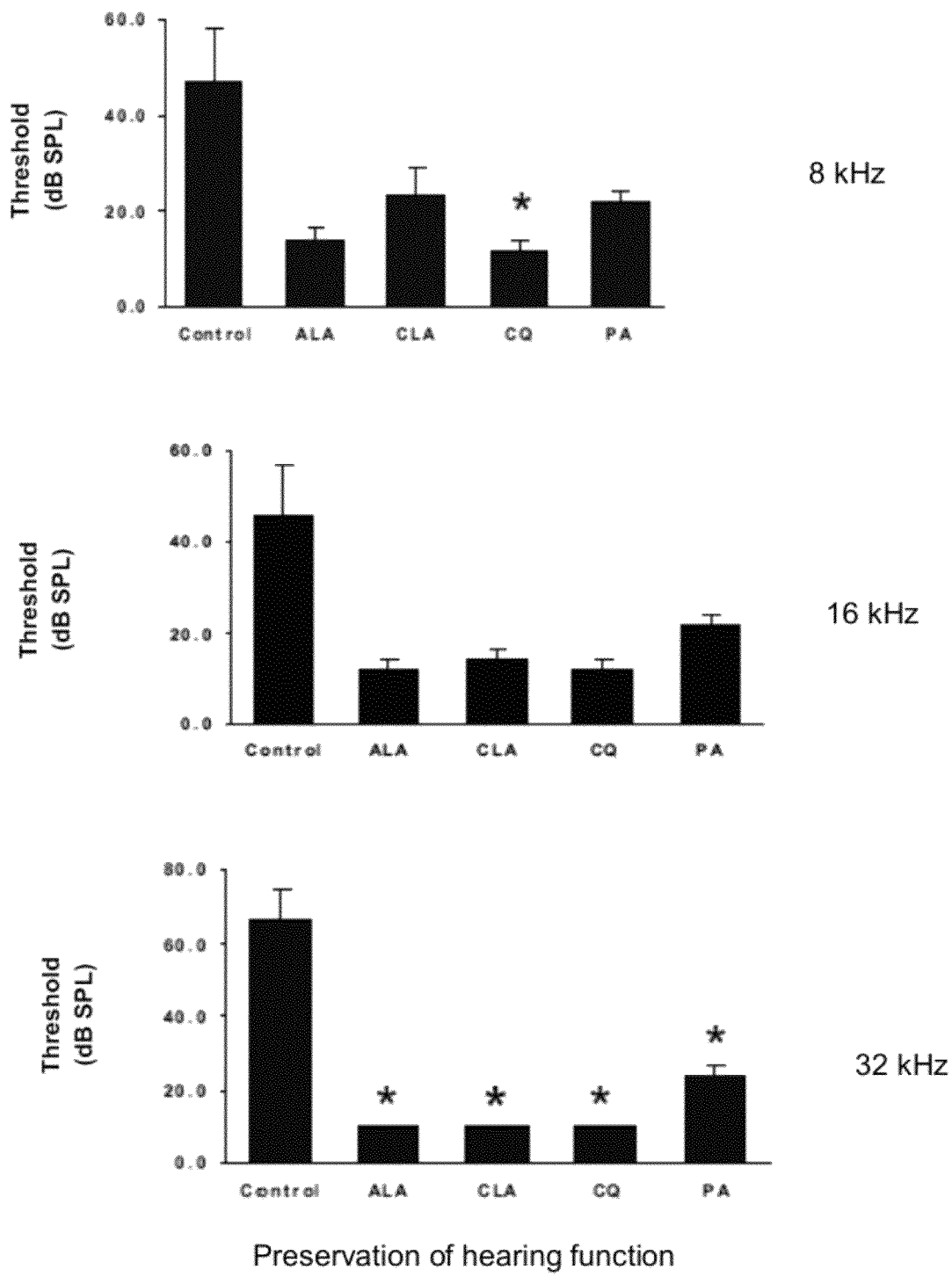
FIG. 2 shows mean ABR thresholds for control, ALA, CLA, CQ and PA mice.

To examine the effects of ALA, CLA, CQ, and PA on presbycusis prevention and treatment, it was examined whether these compounds retard late onset of presbycusis in B6 mice. ABR thresholds measured from these mice revealed that Control mice exhibited moderate age-related hearing loss at 8, 16, 32 kHz (low, mid, and high frequency respectively) (FIG. 2). In contrast, CQ mice displayed normal hearing at 8 and 32 kHz and ALA, CLA, and PA mice displayed normal hearing at 32 kHz (*P<0.05, n=5), showing these compounds prevented the manifestation of presbycusis to this age (FIG. 2).

The effects of the compounds on age-related cochlear degeneration were next investigated. Pathological analysis revealed that the cochleae from Control mice displayed severe loss of hair cells and SGCs (FIG. 3A-B), whereas the cochleae from ALA, CQ, and PA mice displayed no or only a few loss of the hair cells and SGCs (FIG. 3C-H), showing prevention of cochlear degeneration by the compounds. Decreased SGC density is one of the hallmarks of presbycusis in mammals (Keithley et al., [2004], supra). The mean spiral ganglion cell densities of ALA, CQ, and PA mice were significantly higher than that of Control mice (*P<0.05, n=5) (FIG. 4), showing prevention of spiral ganglion neuronal cell loss by the compounds. In summary, this example provides strong evidence that ALA, CLA, CQ, and PA can prevent and treat presbycusis in mammals, and that these compounds can protect critical cochlear cells such as spiral ganglion neurons from age-related degeneration.

Spiral ganglion in cochlea mainly consists of neurons (type I and II neuronal cells). Hair cell receive a sound and pass the sound to spiral gangilion neurons, and it is the spiral ganglion neurons that send the sound information to the brain.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A method of treating presbycusis, comprising:
administering a composition comprising phenylalanine (PA) to a subject having symptoms of presbycusis in sufficient amount to reduce said symptoms.

2. The method of claim 1, wherein said composition comprises one or more additional compounds selected from the group consisting of α-lipoic acid (ALA), conjugated linoleic acid (CLA), and coenzyme Q10 (CQ).

3. The method of claim 2, wherein said one or more additional compounds are ALA and CLA; or CQ and CLA.

4. The method of claim 2, wherein said one or more additional compounds are ALA, CQ and CLA.

5. The method of claim 1, wherein said administering results in reduction in loss of spiral ganglion cells in said subject.

* * * * *